(12) United States Patent
Carpignoli et al.

(10) Patent No.: US 10,086,053 B2
(45) Date of Patent: Oct. 2, 2018

(54) THERAPEUTIC VEGETABLE SUBSTANCES

(71) Applicants: Giuseppe Carpignoli, La Cassa (IT); Alberto Di Giovanni, Cafasse (IT)

(72) Inventors: Giuseppe Carpignoli, La Cassa (IT); Alberto Di Giovanni, Cafasse (IT)

(*) Notice: Subject to any disclaimer, the term of this patent is extended or adjusted under 35 U.S.C. 154(b) by 24 days.

(21) Appl. No.: 15/132,369

(22) Filed: Apr. 19, 2016

(65) Prior Publication Data

US 2016/0228519 A1    Aug. 11, 2016

Related U.S. Application Data

(63) Continuation-in-part of application No. 13/730,204, filed on Dec. 28, 2012, now Pat. No. 9,345,752.

(30) Foreign Application Priority Data

Dec. 6, 2012    (IT) .............................. T02012A01050

(51) Int. Cl.
| | | |
|---|---|---|
| *A61K 38/48* | (2006.01) | |
| *A61K 47/02* | (2006.01) | |
| *A61K 47/22* | (2006.01) | |

(52) U.S. Cl.
CPC .......... *A61K 38/4873* (2013.01); *A61K 47/02* (2013.01); *A61K 47/22* (2013.01); *C12Y 304/22002* (2013.01); *C12Y 304/22032* (2013.01); *C12Y 304/22033* (2013.01)

(58) Field of Classification Search
None
See application file for complete search history.

(56) References Cited

U.S. PATENT DOCUMENTS

| | | |
|---|---|---|
| 4,485,095 A | 11/1984 | Fujisaki et al. |
| 2008/0031980 A1 | 2/2008 | Rodriguez et al. |
| 2010/0254968 A1 | 10/2010 | Desser et al. |

FOREIGN PATENT DOCUMENTS

| | | |
|---|---|---|
| DE | 43 02 060 A1 | 7/1994 |
| EP | 1 103 272 A2 | 5/2001 |
| EP | 2 106 705 A1 | 10/2009 |
| WO | 2009/070818 A1 | 6/2009 |

OTHER PUBLICATIONS

Walker et al., Bromelain reduces mild acute knee pain and improves well-being in a dose-dependent fashion in an open study of otherwise healthy adults, Phytomedicine, 9: 681-686, 2002.*
Beuth, Evidence-based Complementary Oncology: Innovative Approaches to Optimise Standard Therapy Strategies, Anticancer Research, 30 (2010) 1767-1772.
Chobotova et al., Bromelain's activity and potential as an anti-cancer agent: Current evidence and perspectives, Cancer Letters, 290 (2010) 148-156.
Maurer, Bromelain: biochemistry, pharmacology and medical use, CMLS Cellular and Molecular Life Sciences, 58 (2001) 12341245.
Johns Hopkins Medicine, The James Buchanan Brady Urological Institute, Benign Prostatic Hyperplasia, Accessed Aug. 10, 2015, Online at: urology.jhu.edu/prostate/bph.php.
Beuth, Josef, "Proteolytic enzymes therapy in evidence-based complementory oncology: fact or fiction?", Integrative Cancer Therapies, Dec. 2008, vol. 7, No. 4.
"Bromelain" Memorial-Sloan Kettering Cancer enter, retrieved <http://www.mskcc.org/printpdf/node/3204>, Retrived Jul. 29, 2013.
Desser et al. "Oral therapy with proteolytic enzymes decreases excessive TGF-beta levels in human blood." Cancer Chemotherapy and Pharmacology. Jul. 2001, vol. 47.
Fragakis, Allision Sarubin, The Health Professional's Guide to Popluar Dietry Supplements:, America Dietetic Association, pp. 63-68; 2008.
Italian Search Report dated Jul. 30, 2013, issued in Italian Patent Application No. 20121050.
"Proteolytic enzymes." Memorial Sloan-Kettering Cancer Center, Jun. 2001, retrieved <http://www.mskcc.org/cancer-care/herb/proteolytic-enzymes>.
Zavadova et al. Stimulation of reactive oxygen species production and cytotoxicity in human neutrophilis in vitro and after oral administration of a polyenzeyme preparation.: Cancer Biotherapy Summer 1995, vol. 10, No. 2.

* cited by examiner

*Primary Examiner* — Jennifer M. H. Tichy
(74) *Attorney, Agent, or Firm* — Sughrue Mion, PLLC

(57) ABSTRACT

A pharmaceutical product containing papain, bromelain or mixtures thereof is intended for the treatment of several pathologies, such as Alzheimer's disease and depression, at a dosage of at least 7000 mg administered in a single dose. This dosage relates to papain powder having a titre of 3 U/mg and bromelain powder having a titre of 2 U/mg, and to a patient with a body weight of 55 kg. In the case of variations of the titre and/or of the body weight of the patient, the dosage must be adjusted in proportion to said variations.

3 Claims, No Drawings

THERAPEUTIC VEGETABLE SUBSTANCES

This application is a continuation-in-part of U.S. application Ser. No. 13/730,204, filed Dec. 28, 2012 (now U.S. Pat. No. 9,345,752, issued May 24, 2016), and claims priority to Italian Application No. TO2012A001050, filed Dec. 6, 2012, the contents of each are incorporated by reference in their entirety.

TECHNICAL FIELD

The present disclosure relates to the therapeutic use of vegetable substances, and in particular of papain, bromelain and mixtures thereof.

BACKGROUND

Vegetable papain consists of several proteolytic enzymes, whose specific action is the hydrolysis of proteins, producing low molecular weight peptides.

As it is known, the enzymes are catalysts that are extremely active in biological reactions and belong to the chemical category of proteins, with chemical groups that can be of a non-protein nature (apoenzyme, the protein part; coenzyme, the non-protein component, especially vitamins and metals).

The enzymes have the character of specificity, and are named on the basis of the substrate on which they act.

The active site of an enzyme consists of a group of amino acids, which are not necessarily positioned in sequence on the polypeptide chain.

The amino acids are essential for human beings, as they make up the sequences of the proteins, as well as of non-protein peptides.

The amino acids are used by cells as nutrients, and are the basis of fundamental physiological activities. They are molecules that contain a COOH— group and an amino group $NH_2$—, joined to one and the same carbon atom C, the alpha carbon with respect to the carboxyl.

With respect to amino acids, the proteins are polymers of condensation of L,alpha amino acids, joined together in long chains by peptide bonds, with a number of proteins that can be extremely large, with L,alpha amino acids combined in various configurations: unknown, with polypeptide chains of helical shape, with folding of the helices with participation of hydrogen bridges.

About 22 amino acids are present in the human body: 8 of these are considered essential, so defined because they are not produced by the human body, but are only obtained from the diet.

Vegetable papain can be considered to be derived from complexes of amino acids with sequences characteristic of papain: lysine, threonine, valine, thionine, leucine, isoleucine, phenylalanine, histidine, arginine, oxyproline, aspartic acid, serine, glutamic acid, proline, alanine, cystine, tyrosine and others.

In the unripe, acidic fruit of Carica papaya there are 20 of the 22 amino acids, including 7 of the 8 regarded as essential. The phenylalanine contained in Carica papaya is among the precursors of substances with antidepressant action. These elementary amino acids can then naturally give rise to an enormous number of amino acid complexes of high molecular weight that are derived from individual amino acids by interaction of various forces: van der Waals, dipole-dipole interactions, particularly hydrogen bonds, ionic bonds.

SUMMARY

The aim of the present disclosure is to use the properties of papain and of bromelain appropriately for certain therapeutic purposes discussed herein.

This aim is achieved with a product containing papain, bromelain or mixtures thereof for use as a medicinal product at a preferable dosage of at least 7000 mg delivered for at least 30 consecutive days in a single daily dose, said dosage being referred respectively to papain powder having a titre of 3 U/mg and to bromelain powder having a titre of 2 U/mg, and to a patient with a body weight of 55 kg, wherein in case of variations of the titer and/or the body weight of the patient the dosage must be adjusted in proportion to said variation.

"Product containing papain, bromelain or mixtures thereof" means, in the present description, any product, in particular a drug, containing at least one of the aforementioned compounds with any degree of purity or titre and/or mixed with other substances.

It goes without saying that, in the case of variations of the titre and/or of the patient's weight, the dosage must be adjusted in proportion to said variations.

DETAILED DESCRIPTION

Hereinafter, embodiments of the present disclosure are described.

Advantageously, the papain is obtained from the unripe, sour, green fruits of Carica papaya.

Vegetable papain has the following characteristics:
powder with titre of about 3 U/mg,
MW of about 23 000,
where 1 U corresponds to the amount of papain that hydrolyses 1 micromole of N-alpha-benzoyl-L-arginine ethyl ester hydrochloride per minute at pH 6.2 at 25° C. Stable at 2-8° C.

The vegetable bromelain used (from pineapple) has the following characteristics:
powder with titre of about 2 U/mg
MW of about 28 000,
where 1 U corresponds to the amount of bromelain that hydrolyses 1 micromole of 4-nitrophenol per minute at pH 4.6 and 25° C. with the substrate N-alpha-carbobenzoyl-L-lysine-4-nitrophenyl ester.

The product with the dosage of the invention has a therapeutic effect against every form of benign and malignant tumour, both undergoing metastasis, and with low or zero toxicity, and against other non-tumoral diseases, with the warning to avoid the treatment of patients undergoing dialysis and women who are or are suspected of being pregnant.

Among the neoplastic diseases that are treatable, we may mention benign and malignant tumours of any kind, for example of the oral cavity, lymphoma, cerebrocerebellar neoplasias (ependymoma, medulloblastoma, gliomas), of the uterus, fibromas, of the breast, of the vertebral column, of the intestine, of the colon and rectum, of the prostate, lung, gastric, of the liver, of the pancreas, of the gallbladder, of the oesophagus, of the stomach, of the bladder, of the kidney, bone, melanoma, of the ovaries and of the testes.

Among the non-tumoral diseases that are treatable we may mention leukaemias, thyroid, multiple sclerosis, pneumonia, polyarthritis, osteomyelitis, diabetes mellitus, diseases of the circulatory system, diseases of the nervous system, infections of any nature, in particular pulmonary, varicoses, hepatic cirrhosis, leprosy, AIDS, autoimmune diseases, infarction, stroke, ALS and Parkinson's disease.

The product with the dosage of the present invention is usable not only in human beings, but also in animals, as well as concomitantly with other plant or animal enzymes, such as chymotrypsin, trypsin, pancreatin etc., and/or chemotherapeutic, herbal and dietetic agents and drugs, vegetable and synthetic active principles, and food supplements.

According to the invention, the daily dose of papain, bromelain and mixtures thereof is preferably at least 7000 mg, more preferably at least 14000 mg, and even more preferably is between 14000 and 20000 mg. For particularly weak or debilitated patients, having for example low blood pressure or heart disorders, the preferred daily dose is between 5000 and 7000 mg.

If necessary, administration of papain and bromelain can be combined with the administration of specific compounds, which avoid problems connected with the high single dose of administration of papain/bromelain per day (24 hours), and are at the same time able to activate the cellular selectivity directed solely at infected cells and metastases in progress.

These compounds—for example calcium chloride, potassium chloride, sodium chloride, calcium sulphate, silica—can be energized beforehand by exposure to low-intensity magnetic fields and then stabilized.

These compounds in aqueous dilution or dispersion of 1 to 1000 can be administered in amounts between 30 and 70% of that of papain and bromelain, in particular about 50%.

Treatment against carcinogenic cells is initiated with a single dose per day (24 hours), repeating it after 24 hours, then increasing it up to the limit of tolerability of the healthy tissue or organ compared to that which is carcinogenic.

After patients took a single daily dose of 14000-20000 milligrams of papain, values of blood pressure, degree of hydration and heart rate were observed in the normal range, already with results that were positive therapeutically.

It is also possible to administer adjuvant substances simultaneously, such as vitamin C, low doses of cortisone, plant complexes for energy, mineral salts, antiviral and antibacterial agents.

The final result was excellent therapeutically. The values obtained 20/30 days after completion of the whole therapy on subjects who previously had an approximate CEA value between 1000 and 2000, were CEA 2 and CA125 1.5.

The patient receives a quick benefit immediately after beginning administration of the product, even if the analytical test values determined with the current methods are subject to interference and therefore the values are inaccurate during the administrations. It is necessary to wait 20/30 days after the end of the administrations to obtain actual values.

The product according to the dosage of the present disclosure can also be applied at an advanced stage of chemotherapy, radiotherapy, surgery etc.

It can be seen from the foregoing that the present disclosure protects any therapy of every type of benign or malignant tumour undergoing metastasis, as well as of any type of non-cancerous pathology, even not mentioned.

The present disclosure aims to protect the studies and experiments conducted for several years about the use of papain/bromelain, pure or at varying degree of concentration—and optionally with addition of synchronizing compounds, or mixed with other plant or animal enzymes or plant or synthetic active principles, whether or not antitumour, whether or not concomitantly with chemotherapeutic, herbal and dietetic agents and drugs—at a high daily dose never previously investigated or patented, in the treatment of benign or malignant tumours, of the diseases mentioned above and of any other pathology not expressly mentioned, requiring therapeutic application of high daily doses of papain/bromelain that were the subject of the aforementioned research and experiments.

The present patent description aims to protect the production, commercialization, sale to public or private health services or individually of products based on more or less pure papain/bromelain or mixed with any other enzyme or pharmaceutical, chemical, herbal, dietetic product or plant or synthetic active principles, food supplements used at the high daily doses stated above according to the present patent, expressed in pure papain/bromelain or at the concentration already stated above, or other concentration.

As already mentioned, the present disclosure also finds application in the veterinary field, in parallel with all the applications mentioned above for human beings.

The present disclosure aims to protect the production, commercialization, and marketing of drugs, food supplements, herbal products, dietetic products, plant or chemical active principles, based on vegetable papain/bromelain, pure or synchronized, or compounds based on pure vegetable papain/bromelain mixed with other plant or animal enzymes already known for experimentation and commercialization (such as chymotrypsin, trypsin, pancreatin and others) with the intention and indication of using them at the high daily doses mentioned above in pure papain, or pure bromelain, or at various concentrations.

The present disclosure aims to protect the research and experimentation conducted into the therapeutic use of papain/bromelain at high daily dose, not previously patented or investigated, as vegetable papain/bromelain at the concentration specified above (or any other vegetable papain/bromelain at varying concentration, referred to the titre of that according to the present patent, taken daily), also for any type of non-cancerous pathology even not mentioned here.

In particular, a pharmaceutical product containing papain, bromelain or mixtures thereof in a daily dosage of at least 7000 mg in a single dose, has been proven to provide a therapeutic effect on several further pathologies, such as Alzheimer's disease and depression, and further allows one to overcome dependency on drug and stupefacient and to recover memory.

With regard to Alzheimer's disease, good therapeutic results were obtained in respect of the treatment of the disease and the dignity of the patients.

Due to the administration of papain with titre of 3 U/mg, a decrease of amyloid plates and neuro-fibril tangles was obtained. Already at the beginning of the administration, a peptization of these protein cerebral plates with a recovery of memory and a meaningful decrease of the confusion state was noticed.

By administering therapeutic doses, a recovery of acetylcholine was noticed with a strong improvement of the transmission power between the nerve cells. Analyses on spinal liquid, and blood, cerebral TAC and neuro psychological tests were employed. With a daily dose of 7000 mg of papain for a cycle of 30 consecutive days, an improvement of the disease symptoms of 60-70% was obtained on 20 patients who were hospitalized and subjected to a medical treatment according to the EU protocols.

A similar treatment with doses of papain catalyzed by monosodium phosphate brought about very good results of memory recovery, which results were confirmed by electro-encephalographic recording with very high temporal resolution of the somatic-sensorial area. The papain administration brought about a stabilized memory recovery of beyond 60% for the patients who were hospitalized and subjected to a medical treatment according to the EU protocols.

Further tests were conducted in order to investigate the possibility of overcoming depression in adult patients already affected by specific organic diseases such as diabetes, cardio-pathology, and HIV. Such tests provided for administering papain with a titre of 2.5-3 U/mg in a minimum daily dose of 7000 mg for 30 consecutive days, and catalyzed with 22% K and Mg ascorbate. Positive results of 60% were obtained in at least 20 patients affected by depression. Further, it was found that the effectiveness of the treatment was increased if the patient had a positive and confident attitude and, in particular, was supported by his/her own religious faith, such as devotion to the Virgin Mary for Catholics.

By administering papain with a titre of 2.5-3 U/mg with minimum daily doses of 5000-7000 mg, for 35-40 consecutive days, and activated with $MgCl_2$ and irradiated by UV rays, it was noticed that the hemato-encephalic barrier is not any more crossed by the drug which loses its destruction power.

After tests on 18 patients, very good results were obtained on 14 patients, also as high as 80%, whereas meaningful results in terms of detoxifying (lower than 50%) were obtained on the remaining 4 patients, even if not so good as for the other patients.

The results obtained depend also on the psychologically cooperating attitude of the patients.

"All things were made by Him, the Word, the Word of God" (John 1.1).

"Blessed Virgin Mary, Health of the Sick" (Pope Benedict XVI).

Naturally, without prejudice to the principle of the invention, the details of implementation and the embodiments can be varied widely from what is described purely for purposes of illustration, while remaining within the scope of the invention as defined in the appended claims.

What is claimed is:

1. A therapeutic method for treating depression in an adult patient already affected by an organic disease, comprising administering to the adult patient in need thereof a product containing papain at a minimum daily dosage of at least 7000 mg delivered for 30 consecutive days, said dosage being referred to a papain powder having a titer of 3 U/mg, wherein the administration of papain is combined with administration of 22% K and Mg ascorbate as a catalyst; and wherein the organic disease is selected from diabetes, cardio-pathology, and HIV.

2. The therapeutic method according to claim 1, wherein the minimum daily dosage of at least 7000 mg is delivered in a single dose.

3. The therapeutic method according to claim 1 wherein the daily dosage of papain is 7000 mg.

* * * * *